(12) United States Patent
Saito

(10) Patent No.: US 7,483,124 B2
(45) Date of Patent: Jan. 27, 2009

(54) METHOD AND APPARATUS FOR ANALYZING BROMINATED COMPOUNDS

(75) Inventor: Kazumasa Saito, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 23 days.

(21) Appl. No.: 11/510,555

(22) Filed: Aug. 28, 2006

(65) Prior Publication Data

US 2007/0229800 A1   Oct. 4, 2007

(30) Foreign Application Priority Data

Mar. 30, 2006   (JP)   ............... 2006-095032

(51) Int. Cl.
G01N 1/00 (2006.01)
G01N 21/35 (2006.01)
G01N 21/65 (2006.01)

(52) U.S. Cl. ............... 356/38; 356/301; 250/339.07

(58) Field of Classification Search ............ 356/36, 356/38
See application file for complete search history.

(56) References Cited

U.S. PATENT DOCUMENTS

| | | | |
|---|---|---|---|
| 3,584,957 A * | 6/1971 | Polchlopek et al. | ............ 356/38 |
| 4,042,331 A | 8/1977 | Schmidt et al. | |
| 7,271,388 B2 * | 9/2007 | Riess et al. | ............ 250/341.8 |
| 2006/0029182 A1 * | 2/2006 | Tani et al. | ............ 378/45 |
| 2006/0169919 A1 * | 8/2006 | Hong et al. | ............ 250/461.1 |
| 2007/0212787 A1 * | 9/2007 | Riess et al. | ............ 436/73 |

FOREIGN PATENT DOCUMENTS

| | | |
|---|---|---|
| DE | 1 523 001 | 4/1969 |
| DE | 25 58 183 | 7/1977 |
| JP | 2000-241321 A | 9/2000 |
| JP | 2000-292350 A | 10/2000 |
| JP | 2005-283336 A * | 10/2005 |

OTHER PUBLICATIONS

German Office Action, dated May 27, 2008, Application No. DE102006040861.6-52.
"Dangers To Humans And The Environment," Technical University Darmstadt, Nov. 1999, revised May 2005.

* cited by examiner

*Primary Examiner*—F. L Evans
(74) *Attorney, Agent, or Firm*—Westerman, Hattori, Daniels & Adrian, LLP.

(57) ABSTRACT

Analysis is carried out by the steps of putting a sample of an inflammable material on a support formed of a heat resistant material; heating the sample; depositing a combustion gas containing initial evaporation components evaporated and scattered from the sample in an early stage of a combustion process of the sample to an inspected substrate; and inspecting the deposit on the substrate and detecting and analyzing brominated compounds. According to this analysis method, there is provided a method, for analyzing detrimental brominated compounds contained in an inflammable material such as PBB and PBDE, which does not require pre-treatment for preparing a measurement sample but is capable of executing high precision high sensitivity analysis by using an economical apparatus and a simple analytical technology.

24 Claims, 3 Drawing Sheets

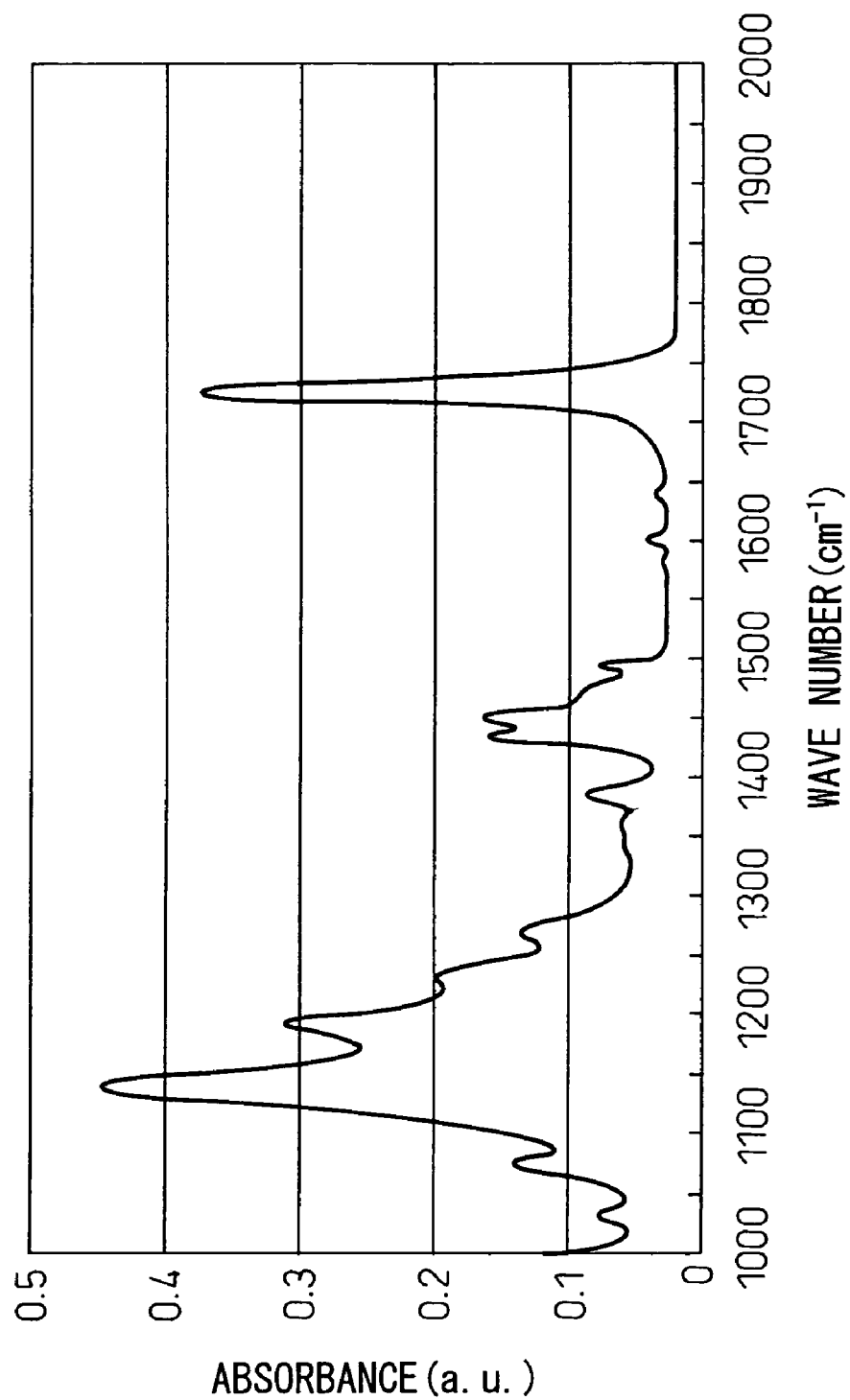

METHOD AND APPARATUS FOR ANALYZING BROMINATED COMPOUNDS

CROSS-REFERENCE TO RELATED APPLICATION

This application is based upon, and claims priority from, Japanese Patent Application No. 2006-095032, filed on Mar. 30, 2006, the contents being incorporated herein by reference.

BACKGROUND OF THE INVENTION

1. Field of the Invention

This invention relates to an analytic technology for bromine-type flame retardants, particularly volatile detrimental compounds contained in the flame retardants, by spectrophotometry such as infrared spectrophotometry and Raman spectrophotometry. More particularly, the present invention relates to a method and an apparatus each used for analyzing, with high accuracy and high sensitivity, those residual organic contaminants which are contained in bromine type flame retardants blended into plastic materials or rubber materials and, among others, polybromobiphenyl (PBB), a polybromodiphenylether (PBDE) such as decabromodiphenylether (DBDE), and other volatile bromine compounds, by using an economical apparatus and a simple analytic technology. The analyzing method and the analyzing apparatus according to the invention are particularly useful for analyzing bromine compounds of bromine-type flame retardants used in plastic members of electronic appliances and home electrical appliances.

2. Description of the Related Art

When members exposed to a high temperature or to a high voltage are formed of plastic materials or synthetic rubber materials in, for example, electronic appliances, home electric appliances and medical equipment, flame retardants have often been blended in these materials. Though various types of flame retardants are known, bromine-type flame retardants such as PBB, PBDE, etc, have drawn increased attention in recent years. This is because these flame retardants not only generate toxic substances (for example, brominated dioxines) equivalent to dioxine when they are burnt at 300 to 600° C. but they may also operate as environmental hormones (hormone disturbing substances).

In view of such serious problems, efforts to the restrict the use of bromine-type flame retardants has proceeded in major countries. A typical example is observed in the EU, that is, "RoHS Directive (Restriction of the Use of Certain Hazardous Substances in Electrical and Electronic Equipment)" enforced on Jul. 1, 2006. This restriction inhibits the use of PBB, PBDE, etc, in electronic and electrical equipment. As a matter of fact, detrimental substances such as PBB and PBDE contained in these products must have a concentration of 1,000 ppm or below. Manufacturers of these products must correctly analyze before the production of the products whether or not plastic materials and the rubber materials contain detrimental substances such as PBB and PBDE.

Technologies for analyzing and detecting flame retardants, and the elements constituting them, in the plastic materials used for producing the electronic appliances and the home electric appliances have been known in the past. For example, Japanese Unexamined Patent Publication (Kokai) No. 2000-292350 describes an identification apparatus for resins, including a small chamber having an open portion at one of the ends thereof, means for thermally decomposing a resin specimen kept in contact with the open portion, means for introducing a decomposition gas generated by the resin specimen into the small chamber and conveying it to infrared spectrophotometry means, and means for comparing and collating the spectrum obtained by the infrared spectrophotometry means with the spectrum of a resin that was generated in advance. By the way, this patent document does not describe the detection of detrimental substances such as PBB and PBDE.

Japanese Unexamined Patent Publication (Kokai) No. 2000-241321 describes a spetrophotometric system, using a thermal decomposition infrared spectrophotometry, which irradiates a laser beam onto a material as an object of spectrophotometry, thermally decomposes the material and acquires infrared absorption spectra from the thermal decomposition gas. Incidentally, this patent document also does not describe the detection of detrimental substances such as PBB and PBDE.

Japanese Unexamined Patent Publication (Kokai) No. 2005-283336 describes the detection of detrimental substances such as PBB and PBDE. This patent document describes an additional substance content judgment program for judging whether or not a predetermined substance (PBDE or PBB) is contained in a measurement object, formed of an unknown plastic material as a base, by utilizing the spectra acquired by subjecting the measurement object to Fourier transform infrared spectrophotometry (FTIR). However, this patent document only teaches use of an unknown plastic as the measurement object.

As can be understood from the facts described above, the prior art technologies for analyzing and detecting the flame retardants in the plastic materials and the elements constituting the flame retardants need complicated constructions for the analyzing apparatus or the analyzing system and an analyzing operation is also extremely complicated. The analysis has a low sensitivity when an economical apparatus and a simple analyzing technology are used. When an expensive apparatus is used, on the contrary, high-sensitivity analysis becomes possible but an expert in analytical technology becomes necessary.

An explanation will be given more concretely. The economical apparatus is an infrared spectrophotometer or a Raman spectrophotometer and can be bought for ¥10,000,000 or less. However, these spectrophotometers can detect the measurement object compounds. such as PBDE and PBB. only when they are contained in an amount of at least 1% by weight in the plastic material, and high sensitivity analysis cannot be expected. Determination is not possible when the infrared peak peculiar to the plastic material and the peak peculiar to the measurement object compound are closed to each other.

On the other hand, a gas chromatography mass spectrograph corresponds to an expensive apparatus and costs as much as ¥20,000,000 or more. When the analysis is conducted by using this mass spectrograph, too, pre-treatment (solvent extraction) is essentially necessary for preparing a measurement sample and the analytic operation is complicated. Further, this mass spectrograph includes the case where a suitable solvent does not exist for the solvent extraction. In such a case, the measurement object compound cannot be detected though the measurement apparatus has a high sensitivity because the compound exists in only an extremely small amount.

SUMMARY OF THE INVENTION

It is an object of the invention to provide an analyzing method and an analyzing apparatus, each being used for analyzing detrimental brominated compounds such as polybromobiphenyl (PBB) and polybromodiphenylether (PBDE) blended as a flame retardant into plastic materials and synthetic rubbers, which do not require pre-treatment for preparing a measurement sample but are capable of high-accuracy and high-sensitivity analysis by using an economical apparatus and a simple analytical technology.

It is another object of the invention to provide an analyzing method and an analyzing apparatus each capable of detecting a brominated compound as a measurement object even when its amount is very small, and also capable of determining the brominated compound even when an infrared peak inherent to a plastic material or synthetic rubber is closed to an infrared peak of the brominated compound, for example.

It is still another object of the invention to provide an analyzing method and an analyzing apparatus each particularly useful for analyzing brominated compounds, such as PBB, PBDE, etc, used as flame retardants, in plastic members and synthetic rubber members in electronic appliances, home electric appliances, medical equipment and other products.

It is still another object of the invention to provide an analyzing method and an analyzing apparatus each useful for providing electronic appliances, home electric appliances, and so forth, that do not contain PBB, PBDE, etc, or contain them in only an amount of 1,000 ppm or less if they do, to respond to the EU RoHS Directive.

The above and other objects of the invention will be understood more readily from the following detailed explanation of the invention.

The inventor of this invention has conducted intensive studies to accomplish the objects described above and has developed the concept that the brominated compounds, used as bromine-type flame retardants, such as PPB and PBDE can be evaporated at a relatively low temperature, and has completed the present invention. In other words, the present invention does not analyze, as such, the to-be-inspected sample such as a plastic material and a synthetic rubber material by the Fourier transform infrared spectrophotometry and does not recover and analyze the combustion gas resulting from the combustion of the sample by infrared spectrophotometry, but employs the steps of heating the sample, depositing brominated compounds evaporated in the early stage of the heating process onto a substrate, and conducts spectrophotometry of the substrate, as the sample, on which the brominated compounds are deposited. The spectrophotometric method includes infrared spectrophotometry by a reflection method or by a transmission method, as examples.

According to one aspect of the invention, there is provided a method for analyzing a brominated compound contained in an inflammable material capable of generating a detrimental brominated compound when it is burnt, comprising the steps of putting a sample of the inflammable material on a support formed of a heat resistant material; heating the sample of the inflammable material; depositing evaporation components evaporated and scattered from the sample during a heating process of the sample onto a substrate; inspecting a deposit on the substrate; and detecting and analyzing the brominated compound.

According to another aspect of the invention, there is provided an apparatus for analyzing a brominated compound contained in an inflammable material capable of generating a detrimental brominated compound when it is burnt, comprising a support, for putting thereon a sample of the inflammable material, formed of a heat resistant material; heating means for heating the sample of the inflammable material, arranged in the proximity of the support; a substrate, for depositing thereto evaporation components evaporated and scattered from the sample during a heating process of the sample, arranged above the support; and an analyzing instrument or appliance for inspecting a deposit on the inspected substrate, and then detecting and analyzing the brominated compound.

As will be understood from the following detailed explanation, the present invention can provide an analyzing method and an analyzing apparatus each being useful for analyzing detrimental brominated compounds such as PBB and PBDE blended as a flame retardant in plastic materials and synthetic rubbers. In contrast with analytical technologies according to the prior art, the method and the apparatus of the invention do not require pre-treatment for preparing a measurement sample but can execute the analysis with high accuracy and high sensitivity by using an economical apparatus and a simple analytical technology. Furthermore, the method and the apparatus of the invention can be advantageously utilized for the analysis of PBB, PBDE, and the like, and can also be utilized advantageously for the analysis of those volatile compounds which evaporate prior to the combustion of the plastic material or the synthetic rubber at the time of heating, and can vaporize.

According to the invention, a large amount of the brominated compound as the measurement object or target need not exist in the plastic material and the synthetic rubber. Even when the amount of the brominated compound is very small, correct detection is still possible. Even when the infrared peak inherent to the plastic material or the synthetic rubber is closed to the infrared peak of the brominated compound, the invention can correctly determine the brominated compound.

The invention can be used particularly advantageously for analyzing brominated compounds as the bromine-type flame retardants used for plastic members and synthetic rubber members of electronic appliances, home electric appliances, medical equipment and other products.

The invention can respond to the RoHS Directive of the EU and to associated restrictions and instructions of other countries, and can contribute to the provision of electronic appliances, home electric appliances, etc, which do not contain PBB or PBDE, or contain which the compounds in an amount of only 1,000 ppm or less.

BRIEF DESCRIPTION OF THE DRAWINGS

FIG. 3 is an infrared spectrum diagram obtained by plotting analytical results for an ABS sheet containing 1 wt % of DBDE in Comparative Example 1.

DESCRIPTION OF THE PREFERRED EMBODIMENTS

The analyzing method and the analyzing apparatus of the brominated compounds according to the present invention can be advantageously executed in various embodiments. Though preferred embodiments of the invention will be hereinafter explained with reference to the accompanying drawings, the invention is not particularly limited thereto.

Figure 1:
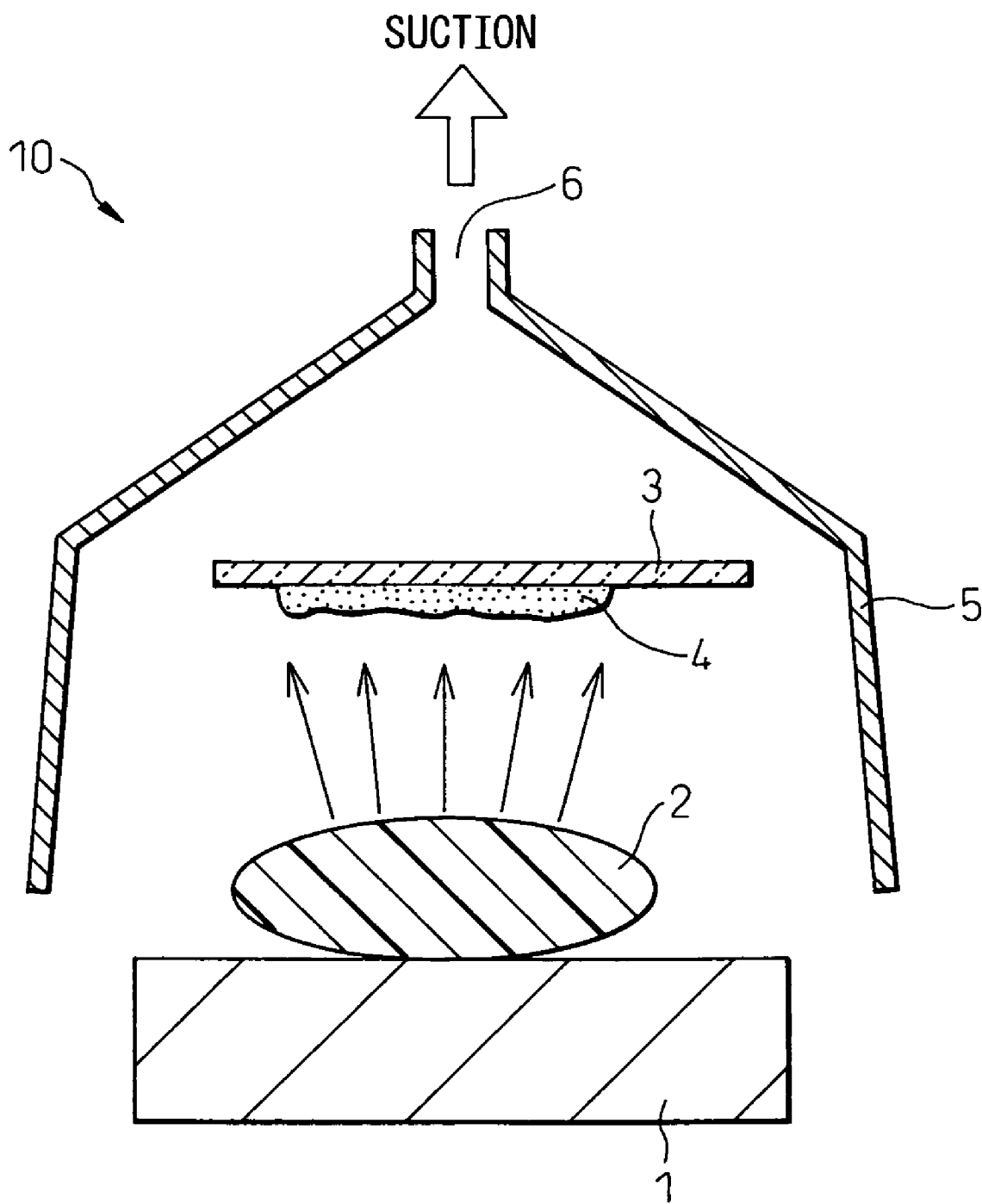
FIG. 1 is a sectional view schematically showing an analyzing apparatus for a bromine-type flame retardant according to a preferred embodiment of the invention.

FIG. 1 schematically shows a preferred embodiment of an apparatus for executing the analyzing method for brominated flame retardants according to the invention. The illustrated analyzing apparatus 10 uses a plastic molding produced by blending bromine type flame retardant (DBDE: decabromodiphenylether) in an ABS resin as a sample 1, and executes a qualitative analysis and determination of DBDE in the plastic molding by using an infrared spectrophotometer. Needless to say, the method and the apparatus according to the invention can be applied to plastic moldings, and other moldings, containing other brominated compounds and volatile compounds in place of DBDE.

Referring to FIG. 1, the sample 2 used in the DBDE analyzing apparatus 10 is a plastic molding produced by blending DBDE with the ABS resin as described above, that is, an inflammable material capable of generating a detrimental brominated compound when it is burnt. Here, the inflammable material is not particularly limited but includes plastic materials, synthetic resin materials and other materials. Suitable examples of the plastic materials, though this is not restrictive, include those resin materials which are customarily used for producing components in electronic appliances and home electric appliances, such as a styrene resin, an ethylene resin and reinforced plastic materials. It is preferred that these inflammable materials do not start to combust when heated for the purpose of evaporating the volatile brominated compound. In other words, the combustion temperature of the inflammable materials is preferably higher than the evaporation temperature of the volatile brominated compounds.

The detrimental brominated compound contained in the inflammable material (the brominated compound need not always be detrimental depending on the intention of analysis) is typically polybromobiphenl (PBP) or polybromodiphenylether (PBDE) that has been generally used in the past as the brominated compound. Needless to say, other volatile compounds can be contained depending on the object of analysis.

The DBDE analyzing apparatus 10 has a support 1 on which the inflammable sample 2 is put. The support 1 is preferably formed of a heat-resistant material capable of withstanding heating of the sample 2. Generally, the support 1 is preferably formed of a ceramic material or heat resistant glass. The shape of the support 1 is not particularly limited but is suitably a flat sheet or a laboratory dish for stably supporting the sample 2.

Various methods may be employed for putting the inflammable sample 2 on the support 1. When a sufficient amount of a deposit of the brominated compound can be deposited on an inspection substrate by heating the sample only once, the necessary sample may well be put on the support. When the amount of the brominated compound contained in the sample is very small, however, the deposit of the brominated compound in the amount necessary and sufficient for the analysis may be deposited onto the inspection substrate by repeating the step of putting the sample on the support and the heating step. In this case, the amount of the brominated compound to be determined can be correctly calculated by dividing the result by the number of samples used. A large number of samples 2 may be put on the support to complete the analysis at one time in place of a repetition of the putting and heating steps.

The DBDE analyzing apparatus 10 is generally equipped with heating means (not shown) for heating the sample 2. Generally, the heating means is preferably arranged in the proximity of the support 1 or below the support 1, for example, but may be built in the support depending on the kind of the heating means (such as nichrome wire).

A hot plate, for example, can be advantageously used as the heating means because it has a simple construction and is easy to handle. The support 1 may be used also as the hot plate or the separately prepared support 1 may be put and used on the hot plate. Examples of a heating means other than the hot plate include an electric heater, an infrared heater and a microwave heater.

In the present invention, the analysis may be carried out batch-wise by putting the sample 2 on the support 1, or by making the support 1 movable, either interruptedly or continuously. For example, a plurality of supports, not shown in the drawing, is put on conveyor means such as a belt conveyor and is allowed to move in the horizontal direction inside the analyzing apparatus. Then, when the sample is put on each support, the samples on the respective supports can be serially heated and analyzed in an interlocking arrangement with the movement of the supports. Here, the conveyor means may guide the supports either interruptedly or continuously in accordance with the object of the analysis and its conditions.

The DBDE analyzing apparatus 10 further includes a substrate 3 above the support 1 in combination with the support 1 on which the sample 2 is put. The substrate 3 is for depositing evaporation components (indicated by an arrow in the drawing) that evaporate and scatter from the sample 2 upon heating of the sample 2. A deposit 4 containing DBDE as its main component is formed on the lower surface of the substrate 3, as shown in the drawing.

The substrate 3 can be formed, of various materials, into an arbitrary shape. When the form of the resulting deposit 4 (that preferably has the form of a thin film) and the handling property in the subsequent analytical steps are taken into consideration, however, the substrate 3 is preferably flat plate-like as shown in the drawing. The flat plate-like substrate 3 preferably has a flat surface having a surface coarseness of 1 μm or below to effectively carry out deposition of the evaporation components. The substrate particularly suitable for carrying out the invention is a glass substrate having such a surface coarseness. A silicon substrate can be used as the substrate, whenever necessary. It is preferred in this case to use a silicon substrate after an oxide film is formed on the surface of the silicon substrate or a hydrophilic treatment is conducted by oxygen plasma treatment, or the like. Furthermore, a substrate coated with a thin gold film on its surface can be advantageously used. The presence of the gold film restricts the reaction with the substrate and the evaporation components with the deposit and makes it possible to carry out the analysis with higher sensitivity.

The substrate 3 is preferably equipped with cooling means (not shown) in the proximity thereof. The cooling means may be built in the substrate 3 or may be arranged on the back of the substrate 3, that is, on the surface opposite to the formation surface of the deposit. Examples of suitable cooling means are a water cooler, dry ice, and so forth. When the cooling means is fitted to the substrate 3, deposition of the evaporation components can be conducted more efficiently on the surface of the substrate 3 and the analysis time can be shortened.

In the DBDE analyzing apparatus 10, the distance between the support 1 and the substrate 3 can be changed in accordance with the shape of the analyzing apparatus, its size and the heating conditions. The gap between them is within the range of about 1 to about 10 cm, for example, but is generally and sufficiently about 5 cm. Therefore, this gap can contribute to a reduction in the size of the apparatus.

Preferably, the DBDE analyzing apparatus 10 further includes a casing or duct 5 to more effectively carry out heating and to prevent scattering of the evaporation components from the sample. After the support 1 and the substrate 3 are generally arranged to oppose each other in such a fashion that the evaporation gas from the sample 2 of the inflammable material on the support 1 exclusively moves towards the deposition surface of the substrate 3 as shown in the drawing, the casing 5 is so constituted as to encompass the support 1 and the substrate 3. In other words, the casing 5 generally defines a cylindrical or circular and conical heating chamber. The casing 5 has an open portion 6 for heating at the upper end of the heating chamber defined by the casing 5. In other words, the casing 5 preferably has a duct-like shape. Preferably, to remove the evaporation gas to the outside of the system, an evaporation gas suction apparatus (not shown) is further arranged at the open portion 6 of the casing 5.

The DBDE analyzing apparatus 10 further includes an analyzing instrument for inspecting the deposit on the substrate and detecting and analyzing the brominated compound contained in the deposit though it is not shown in the drawing. The analyzing instrument is not particularly limited but an infrared spectrophotometer can be advantageously used in view of the fact that the object of detection and analysis is a brominated compound. The infrared spectrophotometer is the one that makes in-situ analysis of the deposit on the substrate, for example, and includes a Fourier-transform infrared spectrophotometer, a far-infrared spectrophotometer and a near-infrared spectrophotometer. A Raman spectrophotometer can be advantageously used in place of the infrared spectrophotometers. Analyzing apparatuses other than the infrared spectrophotometers can be used for detecting and analyzing the brominated compound.

The invention resides also in the method of analyzing the brominated compound contained in the inflammable materials that can generate the detrimental brominated compounds when they are burnt. The analyzing method according to the invention can be executed by using the DBDE analyzing apparatus described above by the steps of putting the sample of the inflammable material on the support formed of a heat-resistant material; heating the sample of the inflammable material; depositing the evaporation components evaporated and scattered from the sample onto the substrate during the heating process of the sample; and inspecting the deposit on the sample and detecting and analyzing the brominated compound.

Each step in the practice of the method of the invention will be readily understood from the foregoing explanation of the DBDE analyzing apparatus.

A supplementary explanation will be given. In the heating step of the sample of the inflammable material, the heating temperature can be varied over a broad range in accordance with the evaporation temperatures of the brominated compound and other volatile compounds contained in the sample and with the combustion starting temperature of the inflammable material. The heating temperature is generally within the range of about 200 to about 300° C. and is preferably within the range of about 240 to about 270° C. Needless to say, the heating step may be carried out at a temperature below 200° C. when the evaporation temperature of the compound as the object of analysis is relatively low.

In the deposition step, the evaporation components evaporated by heating are deposited to the substrate. In this case, the thickness of the deposit is not particularly limited so long as it is a thickness that does not render any problem for the subsequent infrared spectrophotometry. The thickness is generally within the range of about 0.01 to about 10 μm and is preferably at least 1 μm. Incidentally, when a thickness suitable for the analysis is not obtained by single deposition step, it is recommended to use a larger amount of the sample or to repeat the deposition and heating steps.

EXAMPLES

The invention will be subsequently explained with reference to examples thereof. Incidentally, the invention is not, of course, limited to these examples.

Example 1

[Preparation of Sample]
In this example, decabromodiphenylether (DBDE) contained in a trace amount in an ABS resin is analyzed by using the DBDE analyzing apparatus explained previously with reference to FIG. 1.

DBDE in an amount of 10,000 ppm (1.0 wt %) is kneaded with the ABS resin (acrylonitrile-butadiene-styrene copolymer resin) and a sheet substantially having a size of 5 mm in width×5 mm in length×1 mm in thickness is molded. Next, the resulting sheet is put to a freeze pulverizer using liquid nitrogen as a coolant and a fine ABS powder having a particle size of about 0.5 mm or below is prepared. About 5 g of ABS fine powder is placed into a glass laboratory dish and is put on a hot plate set to 270° C.

While the fine ABS powder is heated at 270° C., suction is continued using an accessory air pump. The gas vaporized by heating of the ABS fine powder is gradually deposited to the surface of the glass substrate arranged on the hot plate. After heating is continued for 10 minutes, the heated fine ABS powder is discarded and about 5 g of fine ABS powder (new product) is again put into the glass laboratory dish. Heating is thereafter continued at 270° C. for 10 minutes. The exchange of the ABS fine powder and heating are carried out 5 times in total. Owing to this operation, it can be observed with naked eye that a white material is deposited on the surface of the glass substrate.

Figure 2:
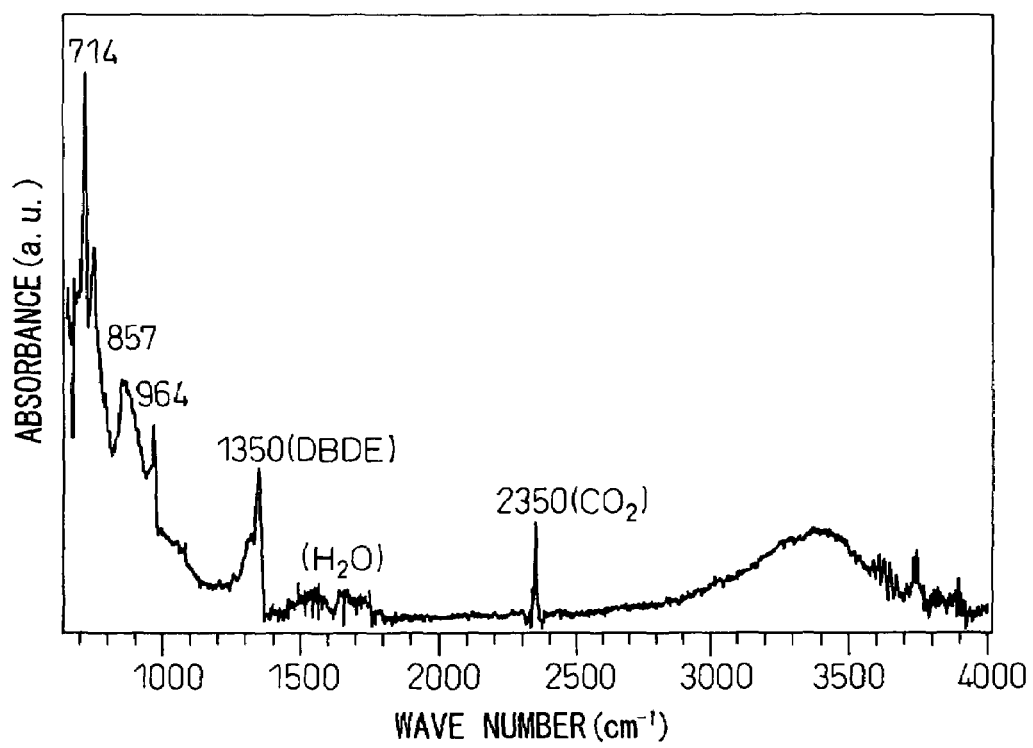
FIG. 2 is an infrared spectrum diagram obtained by plotting the analytical results for DBDE deposited on a glass sheet in Example 1.

[Analysis of Sample]
To determine the white material (sample) obtained in the steps described above, FT-IR (Fourier transform-infrared spectrophotometry) is executed using a total reflection method and a ZnSe crystal. The measurement apparatus used is "Spectrum One B" (trade name), a product of Perkin Elmer Co. An analytical chart plotted in FIG. 2 was obtained as a result of measurement. As can be understood from the chart, the characteristic peak of the volatile compound clearly appears at a wave number 1,350 cm$^{-1}$ and the compound is confirmed to be DBDE.

Comparative Example 1

The procedure of Example 1 is repeated but in this example, the sheet produced in Example 1 and having the substantial size of 5 mm in width×5 mm in length×1 mm in thickness is, as such, used for the purpose of comparison as a measurement sample. When the sample is analyzed by FT-IR, the analytical chart plotted in FIG. 3 is obtained. As can be understood from the chart, a peak cannot be seen at a wave number 1,350 cm$^{-1}$ and whether or not DBDE is contained cannot be determined.

The invention claimed is:
1. A method for analyzing a brominated compound, contained in an inflammable material capable of generating a detrimental brominated compound when it is burnt, comprising:
putting a sample of the inflammable material on a support formed of a heat resistant material;

heating the sample of the inflammable material;

depositing evaporation components evaporated and scattered from the sample during a heating process of the sample onto a substrate; and inspecting a deposit on the substrate, and detecting and analyzing the brominated compound.

2. An analyzing method as defined in claim 1, wherein the deposit on the substrate is in-situ analyzed or analyzed after it is transferred to another place.

3. An analyzing method as defined in claim 1 or 2, wherein the inflammable material is a plastic material or a synthetic rubber material.

4. An analyzing method as defined in claim 3, wherein the plastic material is used for producing a member constituting an electronic appliance.

5. An analyzing method as defined in claim 1 or 2, wherein the brominated compound is polybromobiphenyl or polybromodiphenylether contained in a bromine-type flame retardant.

6. An analyzing method as defined in claim 1 or 2, wherein the substrate is a glass substrate, a silicon substrate having an oxide film on a surface thereof or a substrate having a gold film on a surface thereof.

7. An analyzing method as defined in claim 1 or 2, wherein the substrate is further equipped with cooling means in the proximity thereof.

8. An analyzing method as defined in claim 1 or 2, wherein the support includes heating means in the proximity thereof.

9. An analyzing method as defined in claim 1 or 2, wherein the support is a hot plate or a sample holder member put on a hot plate.

10. An analyzing method as defined in claim 1 or 2, wherein the support is an aggregate of two or more supports each supporting thereon a sample of the inflammable material and guided, either intermittently or continuously, above, heating means arranged below a combustion portion of the sample.

11. An analyzing method as defined in claim 1 or 2, wherein the deposit on the substrate is heated at a temperature of 200 to 300° C.

12. An analyzing method as defined in claim 1 or 2, wherein the deposit on the substrate is in-situ analyzed by infrared spectrophotometry to determine the brominated compound.

13. An analyzing method as defined in claim 1 or 2, wherein the deposit on the substrate is analyzed by a Fourier transform infrared spectrophotometer, a far infrared spectrophotometer, a near infrared spectrophotometer or a Raman spectrophotometer to determine the brominated compound.

14. An analyzing method as defined in claim 1 or 2, wherein the support and the substrate are arranged in such a fashion that the evaporation gas from the sample of the inflammable material on the support exclusively moves towards the deposition surface of the substrate, both of them are encompassed by a casing, an opening is formed at the upper part of the casing, and an evaporation gas suction apparatus is further provided.

15. An analyzing method as defined in claim 1 or 2, wherein the step of putting the sample of the inflammable material on the support formed of the heat resistant material and heating the sample of the inflammable material is repeated, and a deposit, in an amount sufficient for the analysis, is formed on the substrate.

16. An apparatus for analyzing a brominated compound contained in an inflammable material capable of generating a detrimental brominated compound when it is burnt, comprising:

a support for putting thereon a sample of the inflammable material, formed of a heat resistant material; and a substrate for depositing thereon evaporated components evaporated and scattered from the sample during heating of the sample, arranged above the support;

in which a solid deposit formed on the substrate is inspected to detect and analyze the brominated compound, and in which the support and the substrate are arranged to oppose each other in such a fashion that the evaporation gas from the sample of the inflammable material on the support exclusively moves towards the deposition surface of the inspected substrate, both of them are encompassed by a casing defining a circular or a circular and conical combustion chamber and the upper end of the casing has an open portion for exhausting an evaporation gas.

17. An analyzing apparatus as defined in claim 16, wherein the inflammable material is a plastic material or a synthetic rubber material.

18. An analyzing apparatus as defined in claim 17, wherein the plastic material is used for producing a member constituting an electronic appliance.

19. An analyzing apparatus as defined in claim 16 or 17, wherein the brominated compound is polybromobiphenyl or polybromodiphenylether contained in a bromine-type flame retardant.

20. An analyzing apparatus as defined in claim 16 or 17, wherein the substrate is a glass substrate, a silicon substrate having an oxide film on a surface thereof or a substrate having a gold film on a surface thereof.

21. An analyzing apparatus, as defined in claim 16 or 17, wherein the substrate is further cooled in the proximity thereof.

22. An analyzing apparatus as defined in claim 16 or 17, wherein the support is a hot plate or a sample holder member put on the hot plate.

23. An analyzing apparatus as defined in claim 16 or 17, wherein the analyzing of the bromined compound is carried out by using an infrared spectrophotometer for in-situ analyzing the deposit on the substrate.

24. An analyzing apparatus as defined in claim 16 or 17, wherein the analyzing of the bromined compound is carried out by using a Fourier transform-infrared spectrophotometer, a far-infrared spectrophotometer, a near-infrared spectrophotometer or a Raman spectrophotometer.

* * * * *